(12) United States Patent
Wang et al.

(10) Patent No.: US 8,764,954 B2
(45) Date of Patent: *Jul. 1, 2014

(54) SMART SENSOR PORTS AND METHODS OF USING SAME

(75) Inventors: Yi Wang, San Ramon, CA (US);
Benjamin J. Feldman, Oakland, CA (US); Benjamin Rush, Oakland, CA (US); Charlene Haley, Ridgecrest, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1225 days.

This patent is subject to a terminal disclaimer.

(21) Appl. No.: 12/644,468

(22) Filed: Dec. 22, 2009

(65) Prior Publication Data
US 2010/0270149 A1 Oct. 28, 2010

Related U.S. Application Data

(63) Continuation of application No. 12/431,672, filed on Apr. 28, 2009.

(51) Int. Cl.
*G01N 27/416* (2006.01)

(52) U.S. Cl.
USPC ............ 204/403.02; 204/403.01; 204/403.03; 204/403.04; 205/775.5; 205/778

(58) Field of Classification Search
USPC ............... 600/347; 422/50, 76, 82.01, 82.02; 73/53.01; 204/403.01–403.15; 205/777.5, 778, 792
See application file for complete search history.

(56) References Cited

U.S. PATENT DOCUMENTS

| | | |
|---|---|---|
| 4,545,382 A | 10/1985 | Higgins et al. |
| 4,711,245 A | 12/1987 | Higgins et al. |
| 5,262,035 A | 11/1993 | Gregg et al. |
| 5,264,014 A | 11/1993 | Lannefors et al. |
| 5,356,786 A | 10/1994 | Heller et al. |
| 5,509,410 A | 4/1996 | Hill et al. |
| 5,536,249 A | 7/1996 | Castellano et al. |
| 5,593,852 A | 1/1997 | Heller et al. |
| 5,601,435 A | 2/1997 | Quy |
| 5,628,890 A | 5/1997 | Carter et al. |
| 5,820,551 A | 10/1998 | Hill et al. |
| 5,822,715 A | 10/1998 | Worthington et al. |
| 5,899,855 A | 5/1999 | Brown |
| 5,918,603 A | 7/1999 | Brown |
| 5,925,021 A | 7/1999 | Castellano et al. |
| 6,071,391 A | 6/2000 | Gotoh et al. |
| 6,120,676 A | 9/2000 | Heller et al. |
| 6,121,009 A | 9/2000 | Heller et al. |
| 6,143,164 A | 11/2000 | Heller et al. |
| 6,144,837 A | 11/2000 | Quy |
| 6,161,095 A | 12/2000 | Brown |
| 6,175,752 B1 | 1/2001 | Say et al. |
| 6,270,455 B1 | 8/2001 | Brown |
| 6,281,006 B1 | 8/2001 | Heller et al. |

(Continued)

*Primary Examiner* — Luan Van
*Assistant Examiner* — Gurpreet Kaur
(74) *Attorney, Agent, or Firm* — Edward J. Baba; Brian E. Davy; Bozicevic, Field & Francis LLP

(57) ABSTRACT

The present disclosure provides an orientation-nonspecific sensor port for use in analyte meters designed to detect and quantify analyte levels in a fluid sample along with methods of using the same. The present disclosure also provides compositions and methods for facilitating the correct insertion of a sensor into a corresponding analyte meter.

40 Claims, 12 Drawing Sheets

(56) References Cited

U.S. PATENT DOCUMENTS

| | | |
|---|---|---|
| 6,284,478 B1 | 9/2001 | Heller et al. |
| 6,299,757 B1 | 10/2001 | Feldman et al. |
| 6,338,790 B1 | 1/2002 | Feldman et al. |
| 6,377,894 B1 | 4/2002 | Deweese et al. |
| 6,461,496 B1 | 10/2002 | Feldman et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,560,471 B1 | 5/2003 | Heller et al. |
| 6,591,125 B1 | 7/2003 | Buse et al. |
| 6,592,745 B1 | 7/2003 | Feldman et al. |
| 6,600,997 B2 | 7/2003 | Deweese et al. |
| 6,616,819 B1 | 9/2003 | Liamos et al. |
| 6,618,934 B1 | 9/2003 | Feldman et al. |
| 6,638,716 B2 | 10/2003 | Heller et al. |
| 6,676,816 B2 | 1/2004 | Mao et al. |
| 6,730,200 B1 | 5/2004 | Stewart et al. |
| 6,736,957 B1 | 5/2004 | Forrow et al. |
| 6,746,582 B2 | 6/2004 | Heller et al. |
| 6,749,740 B2 | 6/2004 | Liamos et al. |
| 6,764,581 B1 | 7/2004 | Forrow et al. |
| 6,773,671 B1 | 8/2004 | Lewis et al. |
| 6,881,551 B2 | 4/2005 | Heller et al. |
| 6,893,545 B2 | 5/2005 | Gotoh et al. |
| 6,942,518 B2 | 9/2005 | Liamos et al. |
| 7,041,468 B2 | 5/2006 | Drucker et al. |
| 7,138,089 B2 | 11/2006 | Aitken et al. |
| 7,167,818 B2 | 1/2007 | Brown |
| 7,299,082 B2 | 11/2007 | Feldman et al. |
| 7,527,716 B2 | 5/2009 | Harding |
| 2004/0254434 A1 | 12/2004 | Goodnow et al. |
| 2006/0024141 A1 | 2/2006 | Schad |
| 2006/0025662 A1 | 2/2006 | Buse et al. |
| 2006/0091006 A1* | 5/2006 | Wang et al. ............ 204/403.02 |
| 2006/0224141 A1* | 10/2006 | Rush et al. ................. 604/503 |
| 2007/0068807 A1 | 3/2007 | Feldman et al. |
| 2007/0095661 A1 | 5/2007 | Wang et al. |
| 2007/0108048 A1 | 5/2007 | Wang et al. |
| 2007/0199818 A1 | 8/2007 | Petyt et al. |
| 2008/0027301 A1 | 1/2008 | Ward et al. |
| 2008/0066305 A1 | 3/2008 | Wang et al. |
| 2008/0102441 A1 | 5/2008 | Chen et al. |
| 2008/0114280 A1 | 5/2008 | Stafford |
| 2008/0119702 A1 | 5/2008 | Reggiardo |
| 2008/0148873 A1 | 6/2008 | Wang |
| 2008/0267823 A1* | 10/2008 | Wang et al. ................ 422/68.1 |
| 2009/0095625 A1 | 4/2009 | Forrow |
| 2009/0099435 A1 | 4/2009 | Say et al. |

* cited by examiner

SMART SENSOR PORTS AND METHODS OF USING SAME

BACKGROUND

Analytical sensors and meters are often used in chemistry and medicine to determine the presence and/or concentration of a biological analyte of interest. For example, such analytical sensors and meters are used to monitor glucose in diabetic patients and lactate during critical care events.

Many currently available analyte meters are configured such that a sensor is inserted into the analyte meter during the testing process. Such meters are orientation specific in that they require that the corresponding sensor is inserted in a specific orientation which allows for detection of a signal from the sensor and measurement of analyte concentration. This orientation requirement complicates the testing process and, in the context of diabetes care, makes it more difficult for certified diabetes educators to teach the correct use of the devices. This problem may be compounded when the patient is a young child or suffers from impaired vision.

It would therefore be desirable and useful to develop an orientation non-specific analyte meter, capable of performing an accurate and sensitive analysis of the concentration of analytes in a liquid sample.

SUMMARY OF THE INVENTION

The present disclosure provides orientation-nonspecific sensor ports for use in analyte meters designed to detect and quantify analyte levels in a fluid sample along with methods of using the same. The present disclosure also provides compositions and methods for facilitating the correct insertion of a sensor into a corresponding analyte meter. These and other objects, features and advantages of the present disclosure will become more fully apparent from the following detailed description of the embodiments, the appended claims and the accompanying drawings.

BRIEF DESCRIPTION OF THE DRAWINGS

Referring now to the drawings, wherein like reference numerals and letters indicate corresponding structure throughout the several views.

Figure 1:
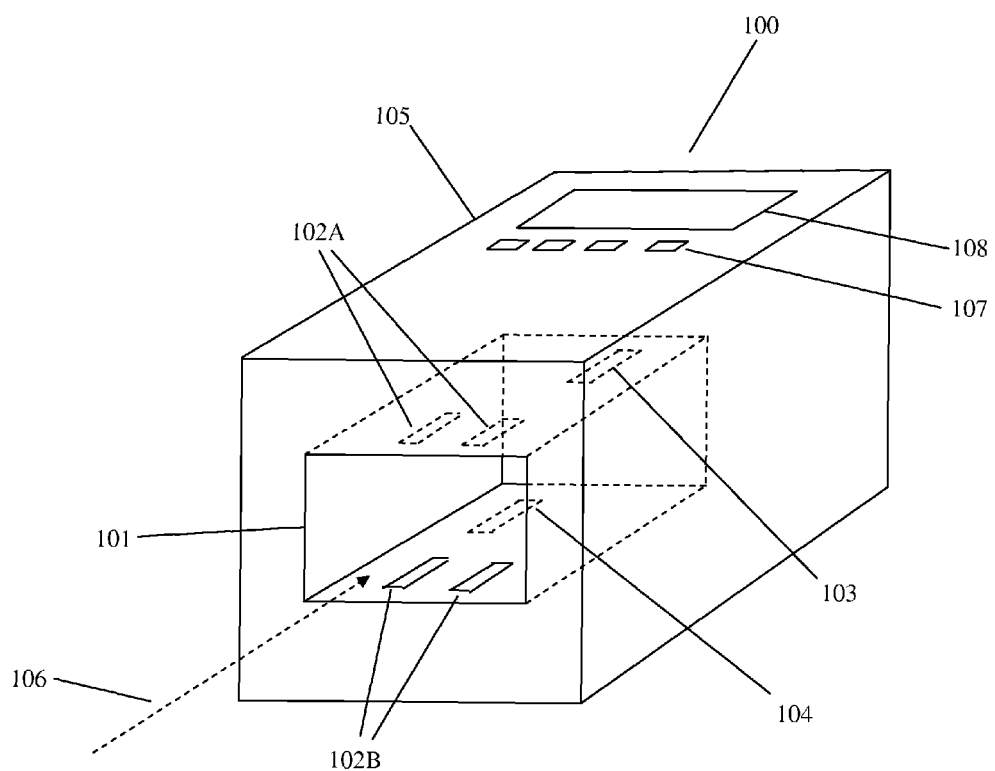
FIG. 1 shows a first embodiment of an analyte meter according the present disclosure.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein and in the appended claims, the singular forms "a," "and," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Analyte Meters

The present disclosure provides analyte meters designed to receive analyte sensors. The analyte meters are configured to process a signal received from the analyte sensor and determine a concentration of analyte based on the received signal. In some embodiments, the analyte meters are specifically designed to receive an analyte sensor in an orientation non-specific manner making it easier for a user to operate the analyte meter and the corresponding sensor.

The analyte meters may be small portable devices designed to be palm-sized and/or adapted to fit into, for example, a pocket or purse of a patient. The analyte meter may have the appearance of a personal electronic device, such as a mobile phone or personal digital assistant (PDA), so that the user may not be identified as a person using a medical device. Additional information is provided in U.S. Pat. No. 7,041,468, titled "Blood Glucose Tracking Apparatus and Method" and in U.S. Patent Application Publication No. US2004/0254434, published Dec. 16, 2004, titled "Glucose Measuring Module and Insulin Pump Combination", the disclosures of each of which are incorporated by reference herein.

In embodiments, the analyte meters may be a larger unit for home use and designed to sit on a shelf or nightstand. In yet other embodiments, the analyte meters may be designed for use in a hospital or doctor's office.

Figure 2:
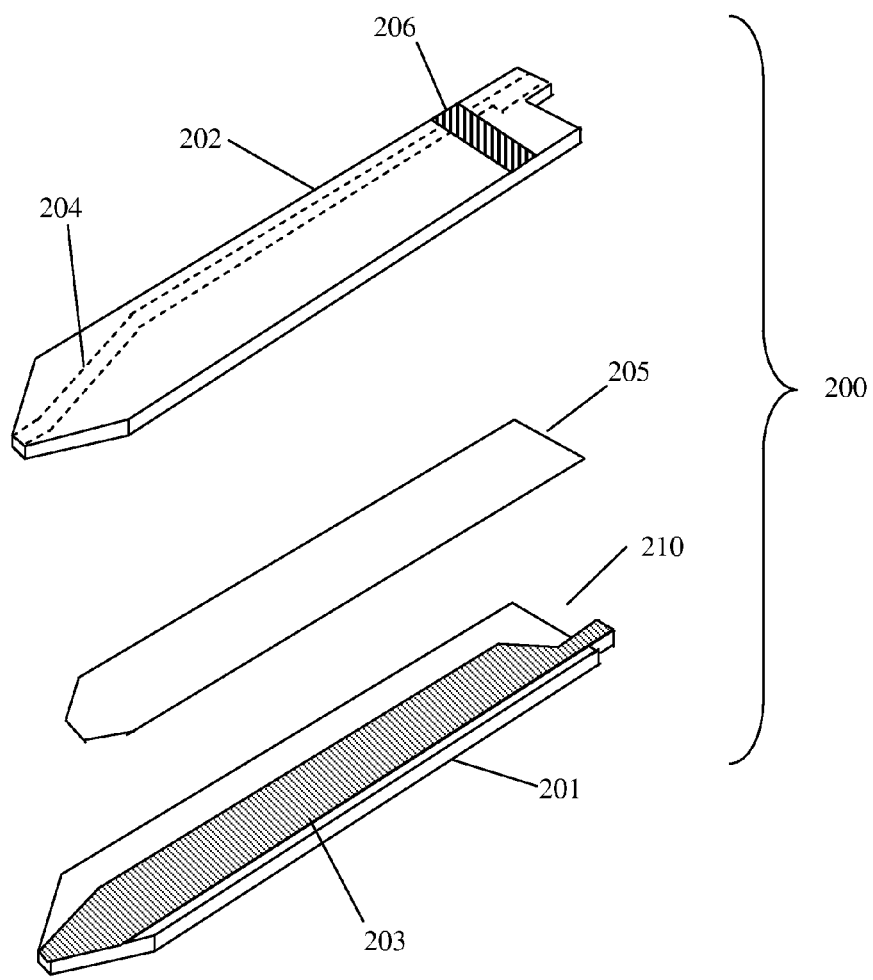
FIG. 2 shows an exploded view of an analyte sensor which is configured such that it can be inserted in two effective orientations into the analyte meter shown in FIG. 1.

Analyte Meter Configured to Receive Analyte Sensor Having an Opposing Electrode Configuration In one embodiment, as illustrated in FIG. 1, analyte meter 100 includes a housing 105 and a sensor port 101 coupled to the housing 105, wherein the sensor port 101 is configured to receive an analyte sensor 200 as shown in FIG. 2. Sensor port 101 includes a first electrode contact 103 and a second electrode contact 104 positioned on opposing faces of sensor port 101. Although electrode contact 103 is designated as the first electrode contact, and electrode contact 104 is designated as the second electrode contact, it should be noted that these designations can be reversed. That is, the electrode contact indicated by reference numeral 104 can be the first electrode contact, and the electrode contact indicated by reference numeral 103 can be the second electrode contact.

Each of the first electrode contact 103 and the second electrode contact 104 is capable of being configured as a working electrode contact. Analyte meter 100 is configured to detect an insertion orientation of analyte sensor 200 upon insertion of analyte sensor 200 into sensor port 101. Based on the detected insertion orientation, analyte meter 100 configures one of first electrode contact 103 and second electrode contact 104 as a working electrode contact. As described in greater detail below, this capability of the analyte meter allows the user of the analyte meter to insert an analyte sensor in either of two effective insertion orientations.

In order to facilitate detection of the insertion orientation of analyte sensor 200, sensor port 101 can optionally be configured to include a first turn-on/selection contact 102A and a second turn-on/selection contact 102B. In the embodiment shown in FIG. 1, these optional turn-on/selection contacts are positioned on opposing faces of sensor port 101, although additional configurations are possible. In one embodiment, as shown in FIG. 1, each of turn-on/selection contacts 102A and 102B includes a pair of conductive strips. This configuration is merely exemplary, and many other configurations including single turn-on/selection contacts are feasible.

In one embodiment, each of first electrode contact 103 and second electrode contact 104 is capable of being configured as a reference and/or counter electrode contact. In such an embodiment, the analyte meter configures one of the electrode contacts as a working electrode contact (e.g., 103) and the other (e.g., 104) as a reference and/or counter electrode contact based on the insertion orientation of the analyte sensor.

In one embodiment, when analyte meter 100 includes optional turn-on/selection contacts 102A and 102B, analyte meter 100 is activated for testing by contacting first turn-on/selection contact 102A or second turn-on/selection contact 102B with analyte sensor 200 upon insertion of analyte sensor 200 into sensor port 101. Analyte meter 100 configures one of first electrode contact 103 and second electrode contact 104 as a working electrode contact and one of first electrode contact 103 and second electrode contact 104 as a reference and/or counter electrode contact based on the contacting of first turn-on/selection contact 102A or second turn-on/selection contact 102B with analyte sensor 200. This allows analyte meter 100 to accept an analyte sensor 200 in either a "face-up" or "face-down" orientation. For example, with reference to FIGS. 1 and 2, analyte sensor 200 can be inserted into sensor port 101 such that working electrode 203 contacts first electrode contact 103. In this orientation, reference and/or counter electrode 204 contacts second electrode contact 104. This insertion orientation is considered a face-up orientation. In a face-down orientation, analyte sensor 200 is inserted such that working electrode 203 contacts second electrode contact 104 and reference and/or counter electrode 204 contacts first electrode contact 103.

Figure 3:
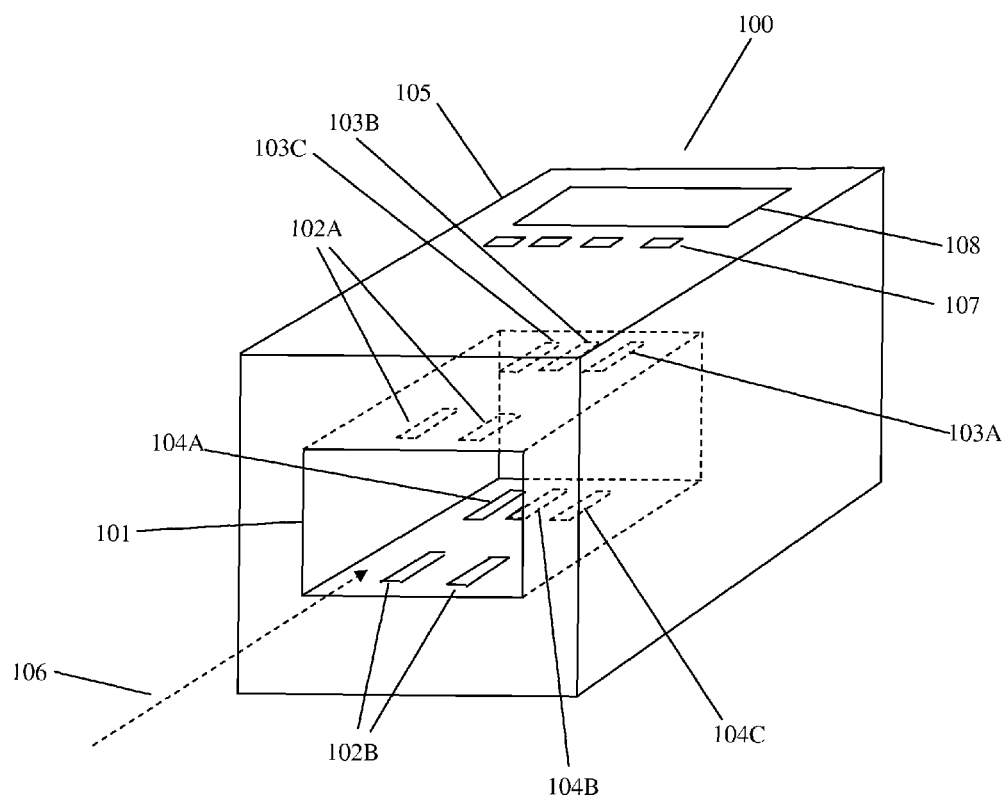
FIG. 3 shows a second embodiment of an analyte meter according to the present disclosure.

FIG. 3 illustrates an embodiment of analyte meter 100, wherein analyte meter 100 is configured to receive an analyte sensor using a four-electrode system having opposing working and reference and/or counter electrodes. Analyte sensors of this type are available from Abbott Diabetes Care Inc., Alameda, Calif. and include FreeStyle® and FreeStyle Lite™ test strips.

As shown in FIG. 3, in one embodiment, an analyte meter 100 according to the present disclosure includes a first set of electrode contacts, including electrode contacts 103A, 103B and 103C; and a second set of electrode contacts, including 104A, 104B and 104C. At least one of electrode contacts 103A, 103B and 103C is capable of being configured as a working electrode contact and at least one of electrode contacts 104A, 104B and 104C is capable of being configured as a working electrode contact.

Figure 4:
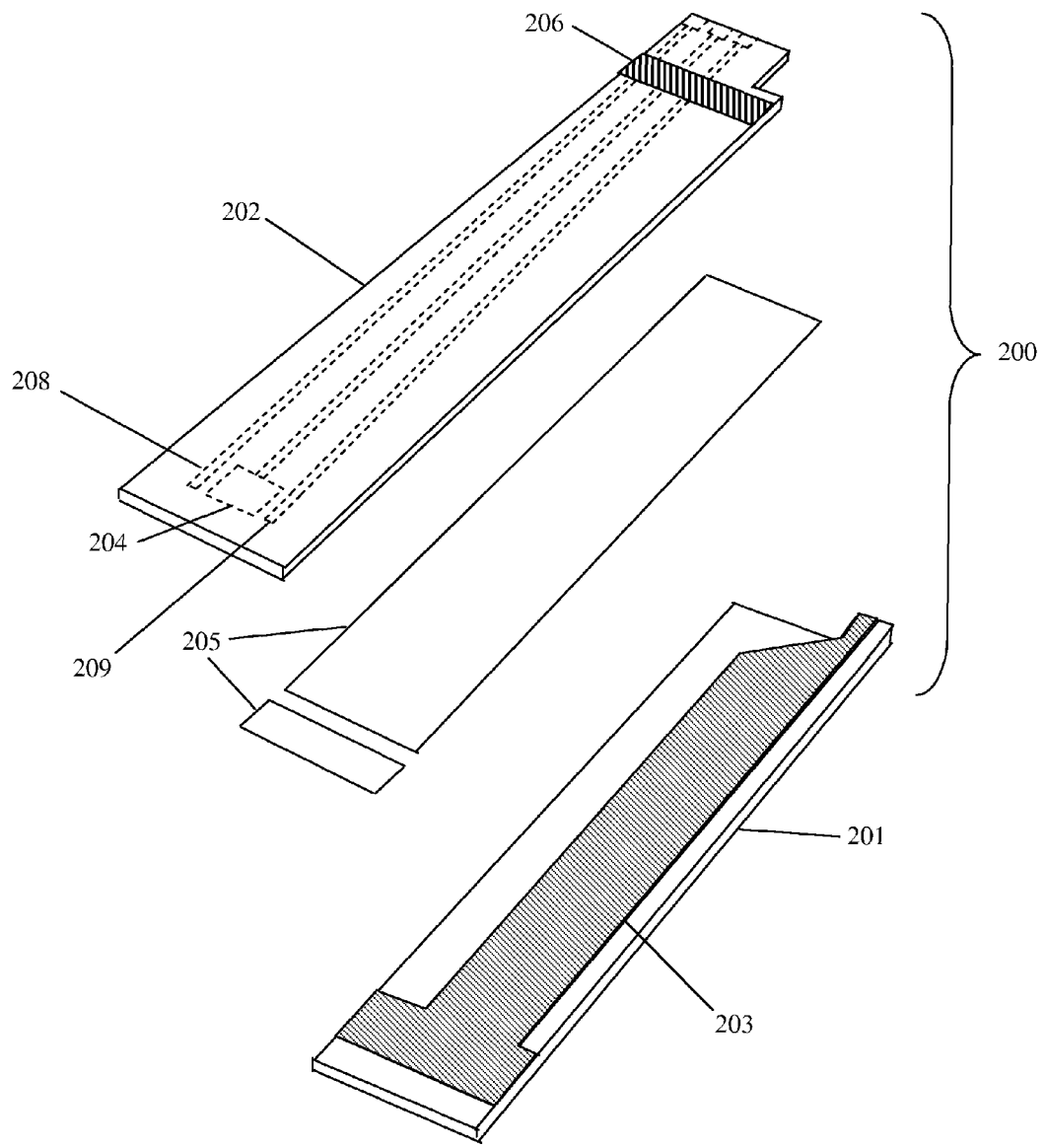
FIG. 4 shows an exploded view of an analyte sensor which is configured such that it can be inserted in two effective orientations into the analyte meter shown in FIG. 3 or FIG. 5.

The analyte meter 100 shown in FIG. 3 is configured to receive an analyte sensor such as analyte sensor 200 shown in FIG. 4. In order to facilitate detection of the insertion orientation of analyte sensor 200, sensor port 101 can optionally be configured to include a first turn-on/selection contact 102A and a second turn-on/selection contact 102B. In the embodiment shown in FIG. 3, these optional turn-on/selection contacts are positioned on opposing faces of sensor port 101, although additional configurations are possible. In one embodiment, as shown in FIG. 3, each of turn-on/selection contacts 102A and 102B includes a pair of conductive strips. As indicated above for FIG. 1, this configuration is merely exemplary, and many other configurations including single turn-on/selection contacts are feasible.

In one embodiment, when analyte meter 100 includes optional turn-on/selection contacts 102A and 102B, analyte meter 100 is activated for testing by contacting first turn-on/selection contact 102A or second turn-on/selection contact 102B with analyte sensor 200 upon insertion of analyte sensor 200 into sensor port 101. As in FIG. 1, the analyte meter 100 shown in FIG. 3 is capable receiving analyte sensor 200 in a "face-up" or "face-down" insertion orientation. For example, with reference to FIGS. 3 and 4, analyte sensor 200 can be inserted into sensor port 101 such that working electrode 203 contacts electrode contact 103A. In this orientation, reference and/or counter electrode 204 contacts electrode contact 104B and indicator electrodes 208 and 209 contact electrode contacts 104A and 104C respectively. This insertion orientation is considered a face-up orientation. In such an orientation, electrode contacts 103C and 103B are inactive. In a face-down orientation, analyte sensor 200 is inserted such that working electrode 203 contacts electrode contact 104A. In this orientation, reference and/or counter electrode 204 contacts electrode contact 103B and indicator electrodes 208 and 209 contact electrode contacts 103A and 103C respectively. In such an orientation, electrode contacts 104B and 104C are inactive.

Figure 5:
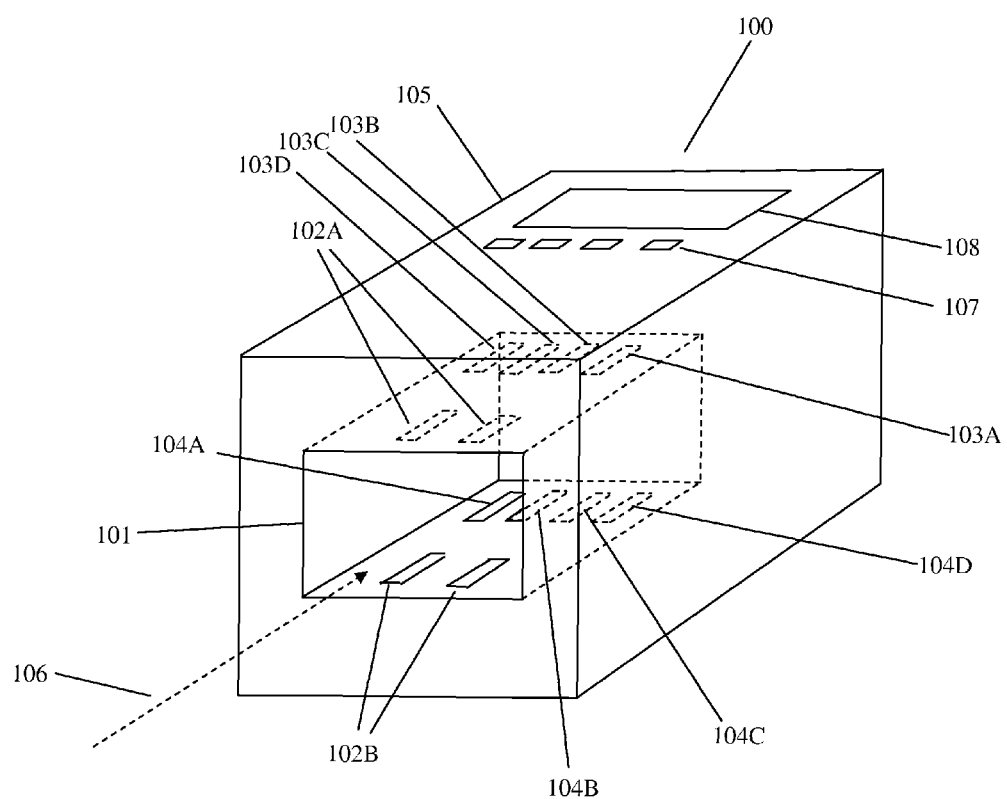
FIG. 5 shows a third embodiment of an analyte meter according to the present disclosure.

In the embodiment shown in FIG. 3, a first set of electrode contacts (103A-103C) are offset relative to a second set of electrode contacts (104A-104C) on opposing faces of sensor port 101. In another embodiment, as shown in FIG. 5, an analyte meter 100 includes a sensor port 101 which includes a first set of contacts (103A-103D) positioned directly across from a second set of electrode contacts (104A-104D) on opposing faces of sensor port 101. As indicated above, a sensor 200 as shown in FIG. 4 can be effectively inserted in either of two insertion orientations into an analyte meter 100 as shown in FIG. 3. An analyte meter 200 as shown in FIG. 4 can also be effectively inserted in either of two insertion orientations into an analyte meter 100 as shown in FIG. 5. In such an embodiment, in a face-up orientation, working electrode 203 contacts electrode contact 103A, reference and/or counter electrode 204 contacts electrode contact 104B, indicator electrodes 208 and 209 contact electrode contacts 104A and 104C respectively, and electrode contacts 103B, 103C, 103D and 104D are inactive. In a face-down orientation, working electrode 203 contacts electrode contact 104A, reference and/or counter electrode 204 contacts electrode contact 103B, indicator electrodes 208 and 209 contact electrode contacts 103A and 103C respectively, and electrode contacts 103D, 104B, 104C and 104D are inactive.

Analyte Meter Configured to Receive Analyte Sensor Having a Coplanar Electrode Configuration The embodiments described above are directed to analyte meters configured to receive analyte sensors having a working electrode positioned in opposition to a reference and/or counter electrode, e.g., as shown in FIGS. 2 and 4. In another embodiment, analyte meters according to the present disclosure are configured to receive analyte sensors having a working electrode and a reference and/or counter electrode positioned in a coplanar configuration. An example of such a coplanar configuration is provided in FIG. 6, wherein electrodes 203, 204, 208 and 209 are positioned in the same lateral plane on substrate 201.

Figure 6:
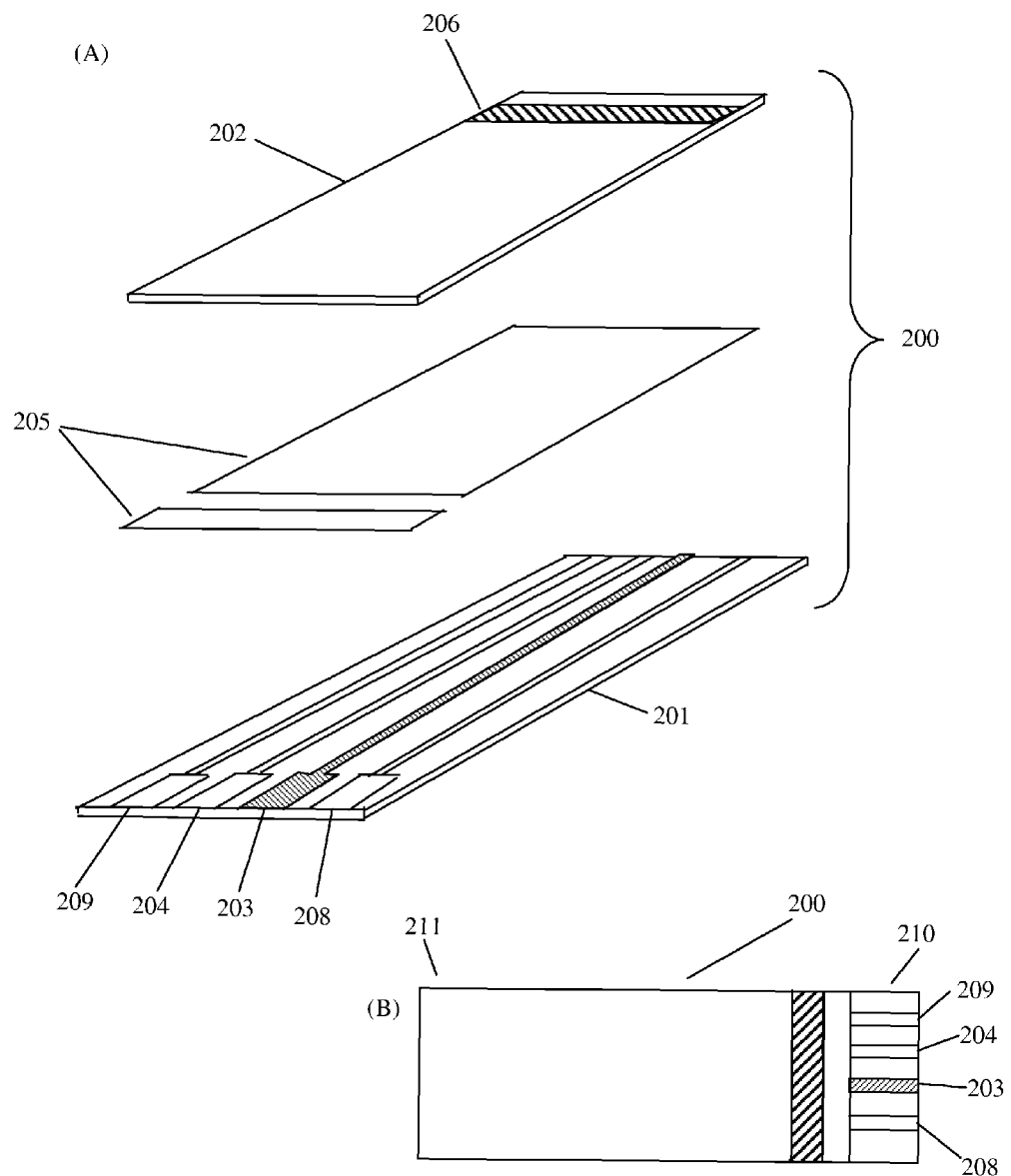
FIG. 6 shows an exploded view (A) and a top view (B) of an analyte sensor which is configured such that it can be inserted in two effective orientations into the analyte meter shown in FIG. 5.

The analyte meter 100 shown in FIG. 5 is configured to receive an analyte sensor such as analyte sensor 200 shown in FIG. 6. In order to facilitate detection of the insertion orientation of analyte sensor 200, sensor port 101 can optionally be configured to include a first turn-on/selection contact 102A and a second turn-on/selection contact 102B. In the embodiment shown in FIG. 5, these optional turn-on/selection contacts are positioned on opposing faces of sensor port 101, although additional configurations are possible. In one embodiment, as shown in FIG. 5, each of turn-on/selection contacts 102A and 102B includes a pair of conductive strips. This configuration is merely exemplary, and many other configurations including single turn-on/selection contacts are feasible.

In one embodiment, when analyte meter 100 includes optional turn-on/selection contacts 102A and 102B, analyte meter 100 is activated for testing by contacting first turn-on/selection contact 102A or second turn-on/selection contact 102B with analyte sensor 200 upon insertion of analyte sensor 200 into sensor port 101. As in FIGS. 1 and 3, analyte meter 100 shown in FIG. 5 is capable receiving analyte sensor 200 in a "face-up" or "face-down" insertion orientation. For example, with reference to FIGS. 5 and 6, analyte sensor 200 can be inserted into sensor port 101 such that working electrode 203 contacts electrode contact 103B. In this orientation, reference and/or counter electrode 204 contacts electrode contact 103C and indicator electrodes 208 and 209 contact electrode contacts 103A and 103D respectively. This insertion orientation is considered a face-up orientation. In such an orientation, electrode contacts 104A, 104B, 104C and 104D are inactive. In a face-down orientation, analyte sensor 200 is inserted such that working electrode 203 contacts electrode contact 104B. In this orientation, reference and/or counter electrode 204 contacts electrode contact 104C and indicator electrodes 208 and 209 contact electrode contacts 104A and 104D respectively. In such an orientation electrode contacts 103A, 103B, 103C and 103D are inactive.

Figure 8:
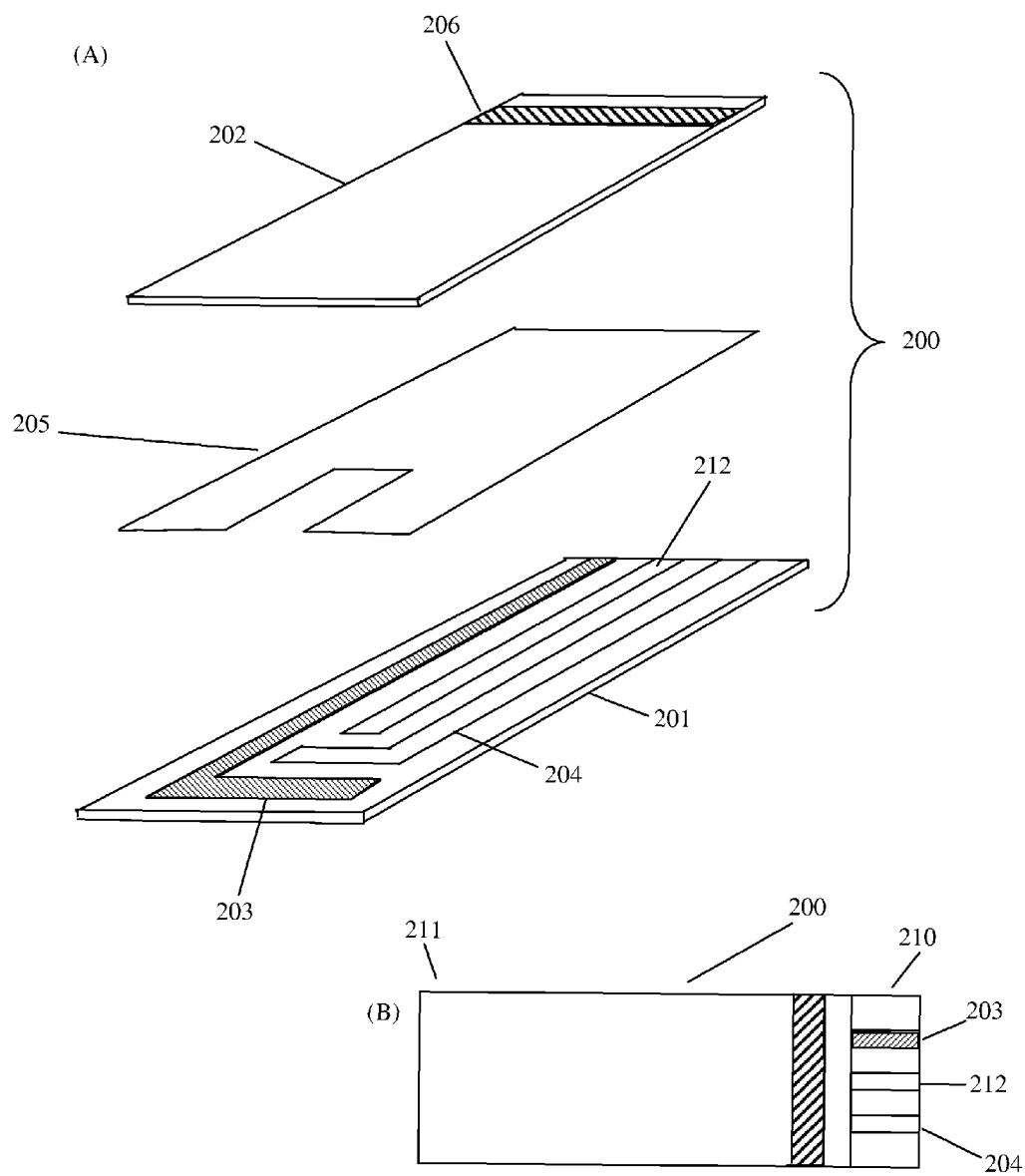
FIG. 8 shows an exploded view (A) and a top view (B) of an analyte sensor which is configured such that it can be inserted in two effective orientations into the analyte meter shown in FIG. 7.

An additional example of a coplanar electrode configuration is provided in FIG. 8, wherein electrodes 203, 204, and 212 are positioned in the same lateral plane on substrate 201.

Figure 7:
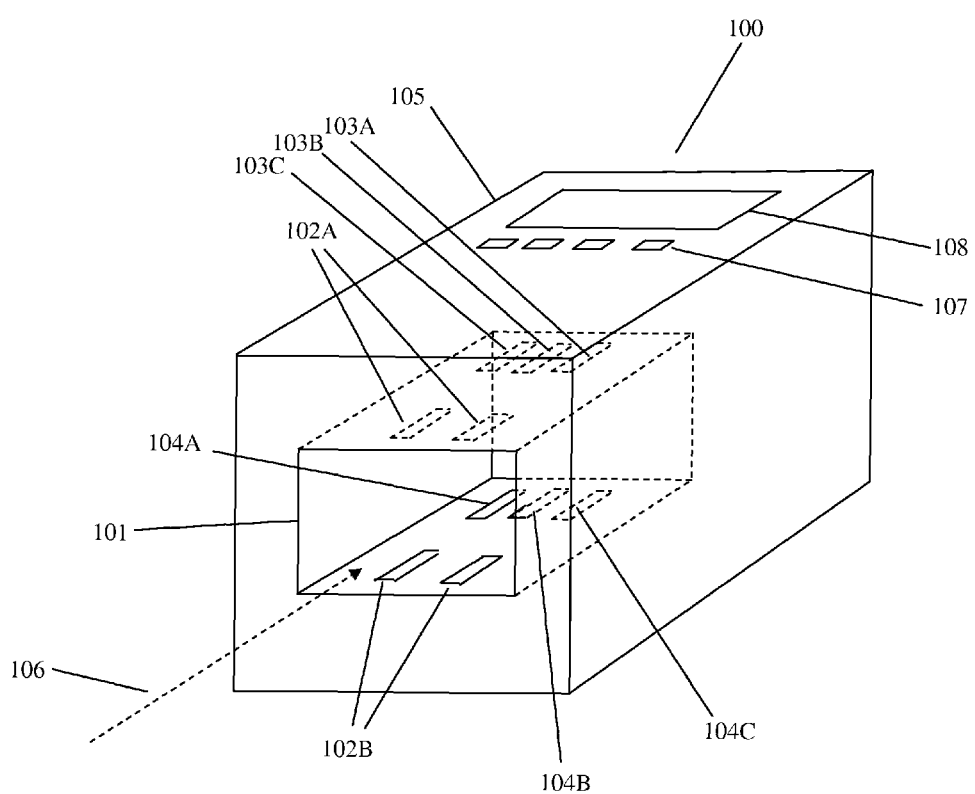
FIG. 7 shows a fourth embodiment of an analyte meter according to the present disclosure.

The analyte meter 100 shown in FIG. 7 is configured to receive an analyte sensor such as analyte sensor 200 shown in FIG. 8. In order to facilitate detection of the insertion orientation of analyte sensor 200, sensor port 101 can optionally be configured to include a first turn-on/selection contact 102A and a second turn-on/selection contact 102B. In the embodiment shown in FIG. 7, these optional turn-on/selection contacts are positioned on opposing faces of sensor port 101, although additional configurations are possible. In one embodiment, as shown in FIG. 7, each of turn-on/selection contacts 102A and 102B includes a pair of conductive strips. This configuration is merely exemplary, and many other configurations including single turn-on/selection contacts are feasible.

In one embodiment, when analyte meter 100 includes optional turn-on/selection contacts 102A and 102B, analyte meter 100 is activated for testing by contacting first turn-on/selection contact 102A or second turn-on/selection contact 102B with analyte sensor 200 upon insertion of analyte sensor 200 into sensor port 101. As in FIGS. 1, 3, and 5 analyte meter 100 shown in FIG. 7 is capable receiving analyte sensor 200 in a "face-up" or "face-down" insertion orientation. For example, with reference to FIGS. 7 and 8, analyte sensor 200 can be inserted into sensor port 101 such that working electrode 203 contacts electrode contact 103C. In this orientation, reference and/or counter electrode 204 contacts electrode contact 103A and indicator electrode 212 contacts electrode contact 103B. This insertion orientation is considered a face-up orientation. In such an orientation, electrode contacts 104A, 104B, and 104C are inactive. In a face-down orientation, analyte sensor 200 is inserted such that working electrode 203 contacts electrode contact 104C. In this orientation, reference and/or counter electrode 204 contacts electrode contact 104A and indicator electrode 212 contacts electrode contact 104B. In such an orientation electrode contacts 103A, 103B, and 103C are inactive.

Additional sensors having coplanar electrode configurations are described in U.S. patent application Ser. No. 12/102,374, filed Apr. 14, 2008, and U.S. Patent Application Publication No. 2009/0095625, the disclosures of each of which are incorporated by reference herein.

Analyte Sensors

Referring to the Drawings in general and FIGS. 2, 4, 6 and 8 in particular, the an analyte sensor 200 described herein generally includes a first substrate 201, a spacer 205, a second substrate 202, a working electrode 203, a reference and/or counter electrode or reference/counter electrode 204, and a measurement zone defined at least in part by working electrode 203, reference and/or counter electrode 204 and one or more of substrate 201, substrate 202 and spacer 205. As used herein, the term "reference and/or counter electrode" refers to an electrode that functions as a reference electrode, a counter electrode or a reference/counter electrode. The measurement zone is configured such that when a sample is provided in the measurement zone the sample is in electrolytic contact with the working electrode 203 and the reference and/or counter electrode and/or reference/counter electrode 204. As shown in FIG. 6, analyte sensor 200 generally includes a proximal end 210 for insertion into analyte meter 100 and a distal end 211 for receiving a liquid sample.

In certain embodiments, an analyte sensor has a generally rectangular shape, i.e., the sensor's length is greater than its width, although other shapes are possible as well. In one embodiment, the analyte sensor is in the form of a strip.

Analyte sensors suitable for use with the analyte meters described herein can include a plurality of electrodes, e.g., 2, 3, or 4 or more electrodes.

In addition to the embodiments specifically disclosed herein, the analyte meters of the present disclosure can be configured to work with a wide variety of analyte sensors, e.g., those disclosed in U.S. patent application Ser. No. 11/461,725, filed Aug. 1, 2006; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. Pat. No. 6,616,819; U.S. Pat. No. 6,143, 164; and U.S. Pat. No. 6,592,745; the disclosures of each of which are incorporated by reference herein.

Fill Indicator Detection

As discussed previously herein, analyte sensor 200 can include one or more indicator electrodes. Such indicator electrodes are well known in the art and can be used to indicate when a measurement zone of analyte sensor 200 is filled with sample. Accordingly, in some embodiments, analyte meter 100 is configured to detect a signal from the indicator electrode in addition to signals from the working electrode 203 and/or reference and/or counter electrode 204.

Suitable signals for detection include, for example, voltage, current, resistance, impedance, or capacitance between the indicator electrode and, for example, working electrode 203. Alternatively, the analyte meter 100 can be configured to detect if a value of the signal (e.g., voltage, current, resistance, impedance, or capacitance) received from analyte sensor 200 has been reached indicating that the measurement zone is filled.

Analyte meter 100 can include a sign (e.g., a visual sign or auditory signal) that is activated in response to the indicator electrode to alert the user that the measurement zone has been filled. The controller unit of analyte meter 100 can be configured to initiate a reading when the indicator electrode indicates that the measurement zone has been filled with or without alerting the user. The reading can be initiated, for example, by applying a potential between the working electrode and the reference and/or counter electrode and beginning to monitor the signals generated at the working electrode. Additional description of indicator electrodes and fill-detection can be found in U.S. Pat. No. 6,592,745, the disclosure of which is incorporated by reference herein.

Turn-on/Selection Monitor

In some embodiments, analyte meter 100 is configured to receive an analyte sensor 200 which includes an optional turn-on/selection monitor 206 as shown in FIGS. 2, 4, 6 and 8. The turn-on/selection monitor 206 is configured to facilitate certain functions of analyte meter 100. For example in one embodiment, turn-on/selection monitor 206 is designed to facilitate detection of analyte sensor 200 by analyte meter 100 upon insertion of analyte sensor 200 into sensor port 101. In one embodiment, such detection results in activation of analyte meter 100 for testing, i.e., turn-on/selection monitor 206 facilitates a "turn-on" function of analyte meter 100. In another embodiment, such detection results in the analyte meter selecting a particular electrode contact (e.g. one of two available electrode contacts) as a working electrode contact, i.e., turn-on/selection monitor 206 facilitates a "selection" function of analyte meter 100.

In the context of the embodiment shown in FIGS. 1, 3, 5 and 7, optional turn-on/selection monitor 206 is designed to contact either first turn-on/selection contact 102A or second turn-on/selection contact 102B upon insertion of analyte sensor 200.

In some embodiments, detection of the analyte sensor is accomplished electrically. For example, the turn-on/selection monitor 206 can be configured to close or open an electrical circuit when the sensor is inserted into the analyte meter. In some embodiments, closing or opening the electrical circuit in turn activates the analyte meter for testing. The turn-on/selection monitor 206 can include a conductive material which facilitates electronic detection of analyte sensor 200. For example, in the embodiment shown in FIGS. 2, 4, 6 and 8, turn-on/selection monitor 206 comprises conductive material is in the form of a conductive strip extending across an exterior surface of analyte sensor 200.

In one embodiment, turn-on/selection monitor 206 is designed such that it physically opens or closes an electric circuit in an analyte meter upon insertion. For example, turn-on/selection monitor 206 could be designed as a dimple or a protrusion which physically opens or closes an electronic circuit upon insertion of the analyte sensor into the analyte meter.

In other embodiments, detection of the analyte sensor is accomplished mechanically. For example, turn-on/selection monitor 206 can have a physical structure which engages with a corresponding physical structure in sensor port 101, e.g., in a "lock and key" type configuration. For example, turn-on/selection monitor 206 can include a first physical structure configured to engage with a second physical structure present in sensor port 101, wherein the physical structure present on analyte sensor 200 includes at least one cutout and/or protrusion, wherein the shape, dimensions and/or number of the at least one cutout and/or protrusion engages with a corresponding physical structure in sensor port 101. The forming of a particular cutout and/or protrusion shape may be accomplished by several methods. For example, the specific cutout and/or protrusion shape may be formed by cutting to a desired shape. The cutting may be done, by, for example, a laser such as a laser-ablation method. The sensor port 101 can be configured such that this physical interaction in turn facilitates turn-on and/or selection functions of the analyte meter 100 as described above.

While the turn-on/selection contacts of FIGS. 1, 3, 5 and 7 are shown as pairs of conductive strips, it should be noted that a variety of configurations are possible for the turn-on/selection contacts, provided that, where the turn-on/selection contacts facilitate a selection function of the analyte meter, the analyte meter can determine which orientation (face-up or face-down) the analyte sensor is in once inserted and select the electrode contacts accordingly.

In one embodiment, where the analyte meter 100 is designed to receive a sensor 200 having a two electrode configuration such as that shown in FIG. 2, one of the electrode contacts is selected as the working electrode contact the remaining electrode contact is selected as the reference and/or counter electrode contact based on the insertion orientation of sensor 200.

In one embodiment, insertion of the analyte sensor 200 into a sensor port 101 of analyte meter 100 results in the completion of a circuit when the turn-on/selection monitor 206 comes into contact with a pair of turn-on/selection contacts.

In one particular embodiment, turn-on/selection monitor 206 is positioned at least substantially perpendicular to working electrode 203 and reference and/or counter electrode 204. In another embodiment, turn-on/selection monitor 206 is positioned at least substantially parallel to working electrode 203 and reference and/or counter electrode 204.

Turn-on/selection monitor 206 may have any suitable configuration, including but not limited to, a stripe extending across analyte sensor 200 from a side edge to a side edge, such as the embodiment shown in FIGS. 2, 4, 6 and 8; a stripe extending across the analyte sensor, although not the entire width; and an array of unconnected dots, strips, or other areas. Other suitable configurations for turn-on/selection monitor 206 are provided in U.S. Patent Application Publication No. US2006/0091006; U.S. Patent Application Publication No. US2008/0267823; U.S. Pat. No. 6,592,745; U.S. Pat. No. 6,143,164; U.S. Pat. No. 6,071,391; U.S. Pat. No. 6,503,381; U.S. Pat. No. 6,616,819 and U.S. Pat. No. 6,893,545; the disclosures of each of which are incorporated by reference herein.

Sensor Port

As described above, analyte meter 100 includes sensor port 101. It should be noted that while the figures depict both analyte sensor 200 and corresponding sensor port 101 as having a rectangular box shape, such configuration is for exemplary purposes only and a variety of other configurations are possible. For example, a cylindrical configuration could be used for both analyte sensor 200 and sensor port 101.

In the embodiment shown in FIG. 1, sensor port 101 includes first electrode contact 103 and second electrode contact 104. These contacts can be made of the same or different material and any suitable material, e.g., carbon, platinum, etc., can be used provided that the material is sufficiently conductive to allow transfer of an electrical signal from electrodes 203 and 204 of analyte sensor 200.

A variety of configurations are possible for electrode contacts 103 and 104, and these configurations can be modified based on the selected configuration of electrodes 203 and 204 on analyte sensor 200 and vice versa. In one embodiment, electrode contacts 103 and 104 are positioned directly across from one another on opposing faces of sensor port 101. In other embodiments, electrode contacts 103 and 104 are not positioned directly across from one another, but are instead offset on opposing faces of sensor port 101. An example of an offset electrode contact configuration is shown in FIG. 1. Notwithstanding the above, electrode contacts 103 and 104 are positioned in the sensor port such that one of electrode contacts 103 and 104 contacts working electrode 103 and the other electrode contact contacts reference and/or counter electrode 204 upon insertion of analyte sensor 200 into sensor port 101.

Sensor port 101 also includes first turn-on/selection contact 102A and second turn-on/selection contact 102B positioned on opposing faces of sensor port 101. These contacts can be made of the same or different material and any suitable material can be used. In some embodiments, the material is sufficiently conductive to allow for completion of an electrical circuit when contacted by a conductive turn-on/selection monitor.

A variety of configurations are possible for turn-on/selection contacts 102A and 102B, and these configurations can be modified based on the selected configuration of turn-on/selection monitor 206 and vice versa. For example, in the embodiments shown in FIGS. 1, 3, 5 and 7, each of turn-on/selection contacts 102A and 102B is shown as a pair of conductive strips positioned on the bottom and top faces respectively of sensor port 101.

Turn-on/selection contacts 102A and 102B can be positioned to suit a particular sensor/meter configuration. In the embodiments shown in FIGS. 1, 3, 5 and 7, turn-on/selection contacts 102A and 102B are positioned substantially parallel with insertion path 106 of analyte sensor 200. This orientation can be adjusted, e.g., depending on the orientation of turn-on/selection monitor 206 on analyte sensor 200. For example, if turn-on/selection monitor 206 were positioned parallel to electrodes 203 and 204 of analyte sensor 200 (rather than perpendicular as shown in FIGS. 2, 4, 6 and 8) it may be desirable to position turn-on/selection contacts 102A and 102B substantially perpendicular to insertion path 106 in sensor port 101. As indicated above, the configuration provided in FIGS. 1, 3, 5 and 7 is merely exemplary, and many other configurations including single turn-on/selection contacts are feasible.

In some embodiments, analyte meter 100 is configured to detect insertion of analyte sensor 200 mechanically. In such embodiments, first turn-on/selection contact 102A and second turn-on/selection contact 102B are configured accordingly. For example, turn-on/selection contacts 102A and 102B could each be designed as a pair of conductive strips, wherein the members of each pair are in contact and part of a closed electrical circuit when analyte sensor 200 is not inserted. The members of each pair can be configured such that their contact is physically disruptable upon insertion of an analyte sensor 200 having a turn-on/selection monitor 206 with a specific physical structure, e.g. a raised protrusion which physically separates a member of each pair of conductive strips from the other member of the pair of conductive strips. In this manner, one of turn-on/selection contacts 102A and 102B will be contacted and the analyte meter 100 can select a particular electrode contact as the working electrode contact accordingly.

In some embodiments, analyte meter 100 is configured to detect insertion of analyte sensor 200 optically. In such embodiments, first turn-on/selection contact 102A and second turn-on/selection contact 102B are configured accordingly. For example, turn-on/selection contacts 102A and 102B could each be configured to include a photodetector, wherein the photodetector is configured to detect a colored area on a face of the sensor. Depending on the insertion orientation, one of turn-on/selection contacts 102A and 102B will detect the colored area and the analyte meter 100 can select a particular electrode contact as the working electrode contact accordingly. A variety of photodetectors are known in the art, including but not limited to photoconductive cells, photodiodes, photoresistors, photoswitches, phototransistors, phototubes, and photovoltaic cells. It is also contemplated that optical means could be utilized to detect a physical structure present on analyte sensor 200, e.g., a particular shape and/or arrangement of cutouts and/or protrusions present on analyte sensor 200, and that insertion orientation could be detected accordingly.

In one embodiment, analyte meter 100 includes an optional illumination device, e.g., a light emitting diode (LED), which may be configured to illuminate the sensor port 101 during the analyte sensor insertion process to assist the user in properly and accurately inserting the analyte sensor 200 into sensor port 101. In some embodiments, the optional illumination device facilitates the optical detection of analyte sensor insertion orientation.

In a further embodiment of the present disclosure, the sensor port 101 may be configured with a physical latch or securement mechanism such that when the analyte sensor 200 is inserted into the sensor port 101, the analyte sensor 200 is retained in the received position within the sensor port 101 until the sample analysis is completed. Examples of such physical latch or securement mechanism may include a unidirectionally biased anchor mechanism, or a pressure application mechanism to retain the analyte sensor 200 in place by applying pressure on one or more surfaces of the analyte sensor 200 within the sensor port 101. Additional information is provided in U.S. Patent Application Publication No. 2008/0119709, the disclosure of which is incorporated by reference herein.

Controller Unit

Analyte meter 100 also includes a controller unit (not shown) coupled to housing 105, wherein the controller unit is configured to process a signal received from analyte sensor 200 and determine the presence and/or concentration of the analyte based on the signal.

The controller unit is configured to process a signal received from analyte sensor 200 and determine a concentration of analyte, e.g., glucose, based on the signal. Details relating to the receipt of an analyte signal from an analyte sensor and the determination of a concentration of analyte are described, for example, in U.S. Pat. No. 7,041,468; U.S. Pat. No. 5,356,786; U.S. Pat. No. 6,175,752; U.S. Pat. No. 6,560,471; U.S. Pat. No. 5,262,035; U.S. Pat. No. 6,881,551; U.S. Pat. No. 6,121,009; U.S. Pat. No. 7,167,818; U.S. Pat. No. 6,270,455; U.S. Pat. No. 6,161,095; U.S. Pat. No. 5,918,603; U.S. Pat. No. 6,144,837; U.S. Pat. No. 5,601,435; U.S. Pat. No. 5,822,715; U.S. Pat. No. 5,899,855; U.S. Pat. No. 6,071,391; U.S. Pat. No. 6,120,676; U.S. Pat. No. 6,143,164; U.S. Pat. No. 6,299,757; U.S. Pat. No. 6,338,790; U.S. Pat. No. 6,377,894; U.S. Pat. No. 6,600,997; U.S. Pat. No. 6,773,671; U.S. Pat. No. 6,514,460; U.S. Pat. No. 6,592,745; U.S. Pat. No. 5,628,890; U.S. Pat. No. 5,820,551; U.S. Pat. No. 6,736,957; U.S. Pat. No. 4,545,382; U.S. Pat. No. 4,711,245; U.S. Pat. No. 5,509,410; U.S. Pat. No. 6,540,891; U.S. Pat. No. 6,730,200; U.S. Pat. No. 6,764,581; U.S. Pat. No. 6,299,757; U.S. Pat. No. 6,461,496; U.S. Pat. No. 6,503,381; U.S. Pat. No. 6,591,125; U.S. Pat. No. 6,616,819; U.S. Pat. No. 6,618,934; U.S. Pat. No. 6,676,816; U.S. Pat. No. 6,749,740; U.S. Pat. No. 6,893,545; U.S. Pat. No. 6,942,518; U.S. Pat. No. 6,514,718; U.S. Pat. No. 5,264,014; U.S. Pat. No. 5,262,305; U.S. Pat. No. 5,320,715; U.S. Pat. No. 5,593,852; U.S. Pat. No. 6,746,582; U.S. Pat. No. 6,284,478; U.S. Pat. No. 7,299,082; U.S. patent application Ser. No. 10/745,878 filed Dec. 26, 2003 entitled "Continuous Glucose Monitoring System and Methods of Use"; U.S. Patent Application No. 61/149,639 entitled "Compact On-Body Physiological Monitoring Device and Methods Thereof", U.S. patent application Ser. No. 11/461,725, filed Aug. 1, 2006; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; and U.S. Patent Application Publication No. 2007/0068807; the disclosures of each which are incorporated by reference herein.

In some embodiments, the analyte meter 100 includes a data storage unit (not shown) operably connected to the controller unit, e.g., as described in U.S. patent application Ser. No. 11/396,182, filed Mar. 31, 2006, titled "Analyte Monitoring Devices and Methods Therefor," the disclosure of which is incorporated by reference herein.

Dosage Calculation Function

In some embodiments, the controller unit is configured to perform medication dosage calculation functions, such as a single-dose calculation function for injection of rapid acting insulin and/or long acting insulin. Analyte meters which include medication dosage calculation functions and methods of performing the dosage calculation functions are described, for example, in U.S. patent application Ser. No. 11/396,182, filed Mar. 31, 2006, titled "Analyte Monitoring Devices and Methods Therefor," the disclosure of which is incorporated by reference herein.

In one embodiment, the controller unit is configured to perform a bolus calculation function. For example, the controller unit may be configured to determine a bolus dosage, e.g., an insulin bolus dosage, based on the signal received from the analyte sensor.

In one embodiment the controller unit is configured to perform an algorithm to determine a medication dosage based on a determined concentration of analyte.

The analyte meter 100 may be configured to automatically enter into a medication dosage calculation mode to, for example, calculate and/or select a medication dosage amount based on information stored in the analyte meter 100 (such as the patient's insulin sensitivity, for example), and/or prompt the patient to provide additional information, such as the amount of carbohydrate to be ingested by the patient for determination of, for example, a carbohydrate bolus dosage determination. The patient may operate the input unit 107 (described in greater below) to provide the appropriate information.

In another embodiment, the analyte meter 100 may be configured to prompt the patient to select whether to retrieve a predetermined or preprogrammed medication dosage amount such as, for example, a correction bolus or a carbohydrate bolus, following the display of the determined analyte concentration from the analyte sensor 200. In this manner, in one embodiment of the present disclosure, analyte meter 100 may be configured to automatically prompt the user or patient to select whether a medication dosage determination is desired following analyte testing using the analyte sensor 200.

Figure 10:
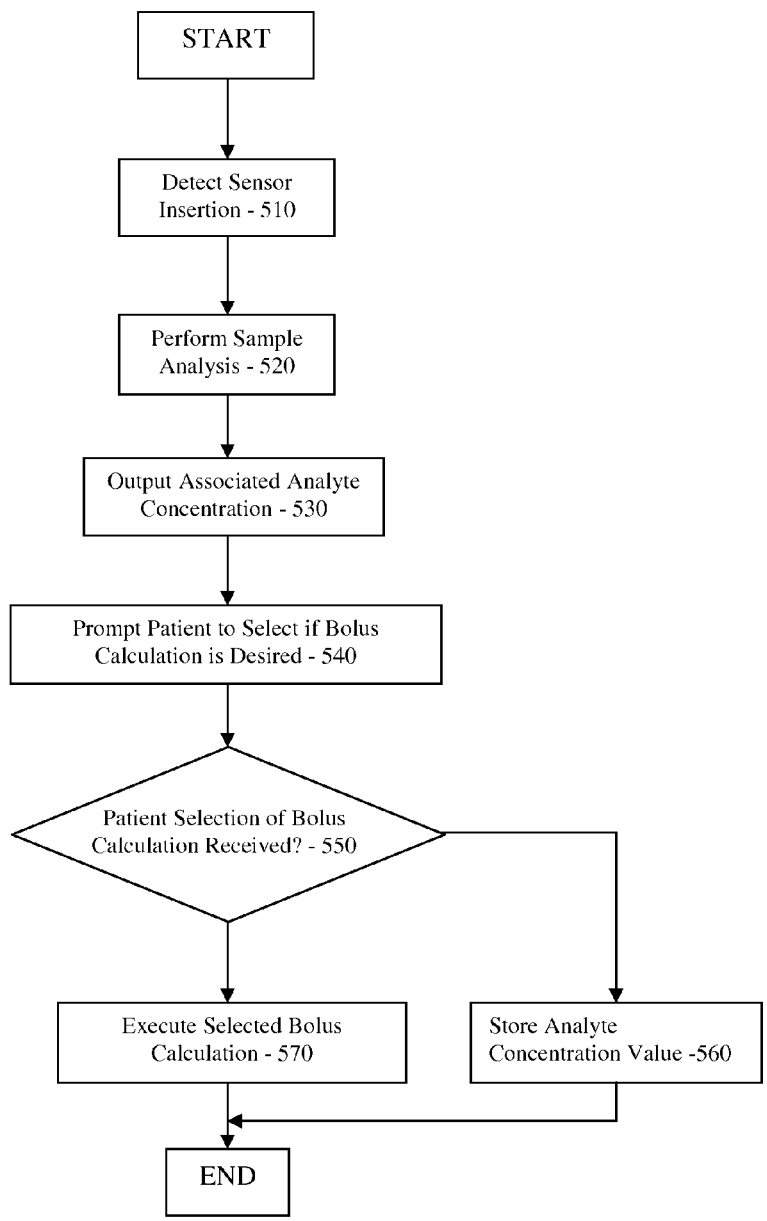
FIG. 10 is a flow chart showing an analyte concentration determination and medication dose calculation procedure in accordance with an embodiment of the present disclosure.

FIG. 10 provides a flowchart illustrating an analyte concentration determination and medication dose calculation procedure in accordance with one embodiment of the present disclosure. Referring to FIG. 10 and FIGS. 1-8, an analyte sensor 200 is detected by the analyte meter 100 (510). Thereafter, the fluid sample, such as a blood sample, present in the measurement zone of analyte sensor 200 is analyzed (520) to determine the corresponding analyte level, such as a glucose level, and the determined analyte level is output (530) on the optional display unit 108 of analyte meter 100, for example, in units of mg/dL.

After determining the analyte level and displaying the measured analyte level to the patient (530), a prompt command is generated and output to the patient to select if the medication dosage calculation is desired (540). More specifically, in one embodiment of the present disclosure, the controller unit is configured to generate a command and display in the optional display unit 108 to query the user as to whether a medication dosage calculation determination is desired by the patient. Thereafter, a determination of whether or not the patient has selected to have the medication dosage calculation performed by the controller unit is made (550). In one embodiment, the patient may operate the optional input unit 107 to select whether or not to have the medication dosage calculation performed.

If it is determined that the patient has selected not to have the medication dosage determination performed, then the determined analyte value is displayed and/or stored (560), e.g., in an optional data storage unit of analyte meter 100, and the routine terminates. For example, in one embodiment, the controller unit may be configured to store the determined analyte value in the optional data storage unit with associated time and/or date information of when the analyte value determination is performed. In an alternate embodiment, the measured analyte value may be stored substantially concurrently with the display of the analyte value.

On the other hand, if it is determined that the patient has selected to have the medication dosage calculation performed, the analyte meter 100 is configured to enter the medication dosage determination mode (570), described in further detail below in conjunction with FIG. 11, where the desired type of medication dosage is determined and provided to the patient.

Figure 11:
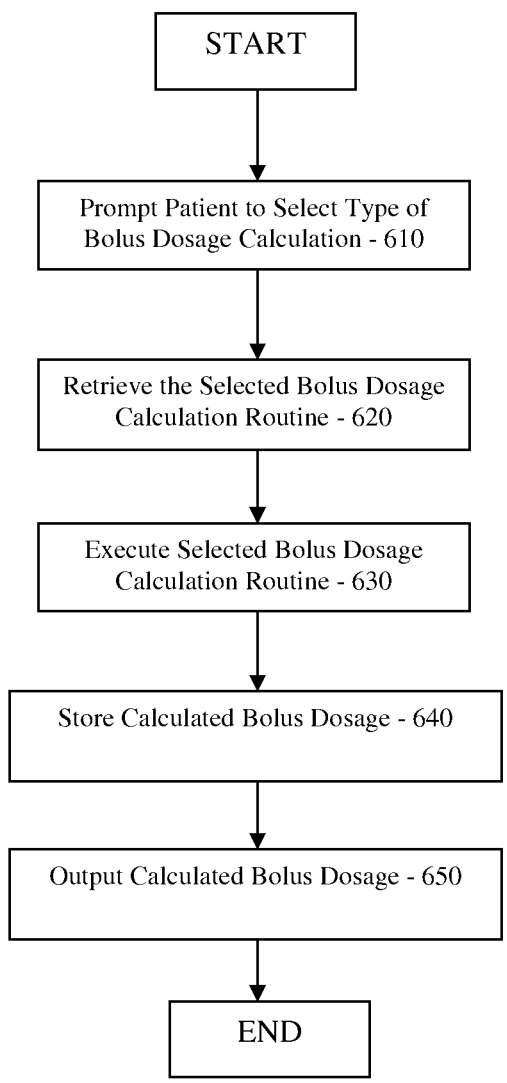
FIG. 11 is a flow chart illustrating the medication dose calculation procedure of FIG. 10.

FIG. 11 is a flowchart illustrating the medication dose calculation procedure of FIG. 10 in accordance with one embodiment of the present disclosure. Referring to FIG. 11 and FIGS. 1-8, when the analyte meter 100 enters the medication dosage determination mode as described above, the controller unit is configured to prompt the patient (for example, by displaying the options to the patient on the optional display unit 108 to select the type of desired medication dosage calculation (610). For example, the controller unit may be configured to output a list of available medication dosage calculation options including, for example, bolus calculation options such as a carbohydrate bolus, a correction bolus, a dual or extended bolus, a square wave bolus, or any other suitable medication calculation function which may be programmed into the analyte meter 100 (and for example, stored in the optional data storage unit).

After the patient selects the desired medication dosage calculation in response to the prompt for medication type selection (610), the selected medication dosage calculation routine is retrieved (620) from the optional data storage unit, and thereafter executed (630). In one embodiment, the execution of the selected medication dosage calculation (630) may include one or more input prompts to the patient to enter additional information as may be required to perform the selected medication dosage calculation.

For example, in the case of calculating a carbohydrate bolus, the patient may be prompted to provide or enter an estimate of the carbohydrate amount that the patient is planning on ingesting. In this regard, a food database may be stored in the optional data storage unit or elsewhere for easy access (e.g., a PC, PDA, telephone, or the like and to which the analyte monitor may be coupled (e.g., wirelessly or by physical connection) to easily retrieve such information) to conveniently determine the corresponding carbohydrate amount associated with the type of food which the patient will be ingesting. Alternatively, the patient may provide the actual estimated carbohydrate count if such information is readily available by the patient.

In the case of calculating a dual bolus of insulin, the patient is prompted to provide, in addition to a dose amount, a time duration information for the extended portion of the bolus dosage to be infused or otherwise delivered to the patient. Similarly, the patient may further be prompted to provide insulin sensitivity information, and any other information as may be necessary to determine the selected bolus dosage amount in conjunction with other relevant information such as insulin on board information, and the time of the most recently administered bolus (so as to provide a warning to the patient if a bolus dosage has been administered within a predetermined time period, and a subsequent administration of the additional bolus dosage may potentially be harmful).

After the execution of the selected medication dosage calculation routine (630), the calculated medication dosage amount is stored (640) in the optional data storage unit, and the calculated medication dosage amount is output displayed to the patient (650) on the display unit 108 of the analyte meter 100, or audibly if the analyte meter is so configured. In certain embodiments, storing and output displaying the calculated medication dosage amount may be substantially concurrently performed, rather than sequentially.

Figure 12:
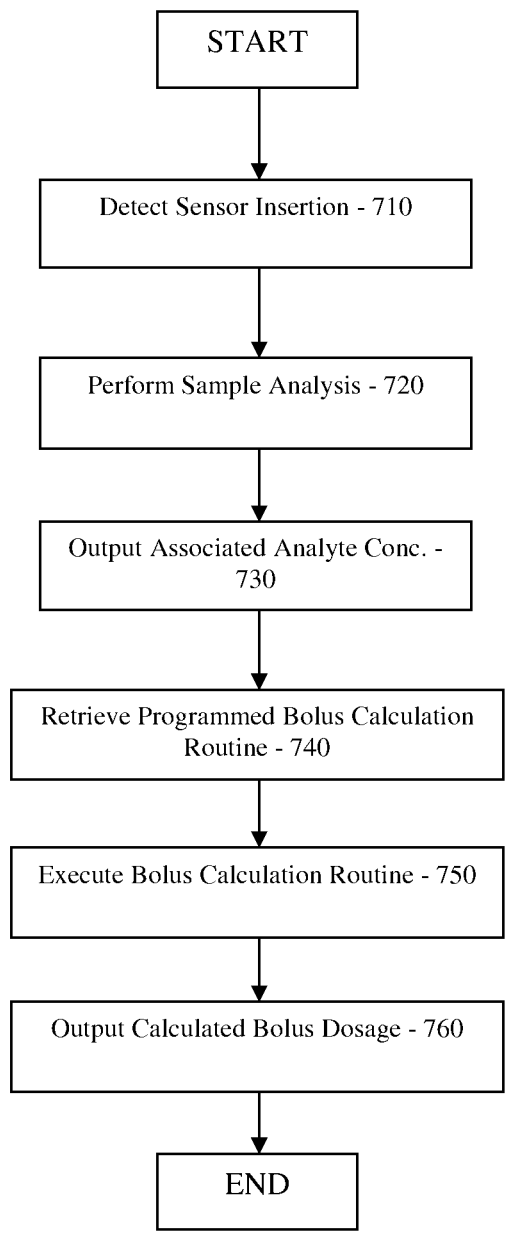
FIG. 12 is a flow chart showing an analyte concentration determination and medication dose calculation procedure in accordance with an alternative embodiment of the present disclosure.

FIG. 12 is a flowchart illustrating an analyte level determination and medication dose calculation procedure in accordance with another embodiment of the present disclosure. An analyte sensor 200 is inserted into the sensor port 101 of analyte meter 100 (710), the fluid sample in the measurement zone of analyte sensor 200 is analyzed to determine the corresponding analyte concentration (720), and thereafter, output displayed (730).

The controller unit is configured to enter into the medication dosage determination mode, retrieve a programmed or predetermined bolus calculation routine (740), execute the pre-programmed or predetermined bolus calculation routine (750), and thereafter, output display the calculated medication dosage amount (760). In this manner, in one embodiment of the present disclosure, the analyte meter 100 may be programmed or configured to automatically enter into the medication dosage determination mode upon completion of the fluid sample analysis for analyte level determination.

In one embodiment of the present disclosure, the analyte meter 100 may be configured to execute different types of medication dosage calculations based on the patient specified parameters. For example, the analyte meter 100 may be configured to perform a carbohydrate bolus determination when the analyte sensor sample analysis is performed within a predetermined time period of a meal event. For example, the analyte meter 100 may be programmed by the patient to automatically select the carbohydrate bolus determination if the analyte sensor fluid sample analysis is performed within one hour prior to a meal time (which may be programmed into the analyte meter 100).

Integrated Medication Delivery System

In some embodiments, analyte meter 100 includes an optional medication delivery device or system (not shown). Additional information regarding medication delivery devices or systems, such as, for example, integrated systems, are provided, for example, in U.S. Patent Application Publication No. US2006/0224141, published on Oct. 5, 2006, titled "Method and System for Providing Integrated Medication Infusion and Analyte Monitoring System", and U.S. Patent Application Publication No. US2004/0254434, published on Dec. 16, 2004, titled "Glucose Measuring Module and Insulin Pump Combination," the disclosure of each of which is incorporated by reference herein. Medication delivery devices which may be provided with analyte meter 100 include, e.g., a needle, syringe, pump, catheter, inhaler, transdermal patch, or combination thereof.

The medication delivery device or system may be in the form of a drug delivery injection pen such as a pen-type injection device incorporated within housing 105 of analyte meter 100. Additional information is provided in U.S. Pat.

Nos. 5,536,249 and 5,925,021, the disclosure of each of which is incorporated by reference herein.

The medication delivery system may be used for injecting a dose of medication, such as insulin, into a patient based on a prescribed medication dosage, and may be automatically updated with dosage information received from the controller unit (not shown) of analyte meter 100. In another embodiment, the medication dosage of the medication delivery system may include manual entry of dosage changes made through, for example, optional input unit 107 coupled to the housing of analyte meter 100. Medication dosage information associated with the medication delivery system may be displayed on an optional display unit disposed on housing 105 of analyte meter 100.

Analyte Detection Systems

An analyte meter 100 as described herein can be a component of one or more analyte detections systems. For example, an analyte detection system according to the present disclosure can include an analyte meter 100 as described herein in addition to one or more sample acquisition and/or testing elements known in the art. In one embodiment, an analyte detection system according to the present disclosure includes an analyte sensor, e.g., an analyte sensor 200 as described herein, and a lancet. In some embodiments, the analyte sensor 200 is in the form of a test strip.

In some embodiments, a lancet and an analyte sensor 200 in the form of a test strip are integrated into the housing of the analyte meter 100. In specific embodiments, a plurality of analyte sensors and a plurality of lancets are integrated into the housing of an analyte meter 100. In other embodiments, the lancet and the test strip are not integrated into the housing of the analyte meter, but are instead included in the system as separate components.

Where the test strip is integrated into the housing of an analyte meter 100, the housing can be configured to hold one or more cartridges or magazines containing test strips to be used in the operation of the system. Similarly, where the lancet is integrated into the housing of an analyte meter 100, the housing can be configured to hold one or more cartridges or magazine containing lancets to be used in the operation of the system.

Additional systems incorporating the analyte meters described herein will be readily apparent to those of ordinary skill in the art upon reading the present disclosure.

Integrated Monitoring Device

In one embodiment, the analyte meter 100 incorporates an optional continuous analyte monitoring device, e.g., a continuous glucose monitoring device (CGM). The continuous analyte monitoring device can be, e.g., a transcutaneously implanted sensor which continually or substantially continually measures an analyte concentration of a bodily fluid. Examples of continuous analyte monitoring systems and devices are described in U.S. Pat. No. 5,356,786; U.S. Pat. No. 6,175,752; U.S. Pat. No. 6,560,471; U.S. Pat. No. 5,262,035; U.S. Pat. No. 6,881,551; U.S. Pat. No. 6,121,009; U.S. Pat. No. 7,167,818; U.S. Pat. No. 6,270,455; U.S. Pat. No. 6,161,095; U.S. Pat. No. 5,918,603; U.S. Pat. No. 6,144,837; U.S. Pat. No. 5,601,435; U.S. Pat. No. 5,822,715; U.S. Pat. No. 5,899,855; U.S. Pat. No. 6,071,391; U.S. Pat. No. 6,120,676; U.S. Pat. No. 6,143,164; U.S. Pat. No. 6,299,757; U.S. Pat. No. 6,338,790; U.S. Pat. No. 6,377,894; U.S. Pat. No. 6,600,997; U.S. Pat. No. 6,773,671; U.S. Pat. No. 6,514,460; U.S. Pat. No. 6,592,745; U.S. Pat. No. 5,628,890; U.S. Pat. No. 5,820,551; U.S. Pat. No. 6,736,957; U.S. Pat. No. 4,545,382; U.S. Pat. No. 4,711,245; U.S. Pat. No. 5,509,410; U.S. Pat. No. 6,540,891; U.S. Pat. No. 6,730,200; U.S. Pat. No. 6,764,581; U.S. Pat. No. 6,299,757; U.S. Pat. No. 6,461,496; U.S. Pat. No. 6,503,381; U.S. Pat. No. 6,591,125; U.S. Pat. No. 6,616,819; U.S. Pat. No. 6,618,934; U.S. Pat. No. 6,676,816; U.S. Pat. No. 6,749,740; U.S. Pat. No. 6,893,545; U.S. Pat. No. 6,942,518; U.S. Pat. No. 6,514,718; U.S. Pat. No. 5,264,014; U.S. Pat. No. 5,262,305; U.S. Pat. No. 5,320,715; U.S. Pat. No. 5,593,852; U.S. Pat. No. 6,746,582; U.S. Pat. No. 6,284,478; U.S. Pat. No. 7,299,082; U.S. patent application Ser. No. 10/745,878 filed Dec. 26, 2003 entitled "Continuous Glucose Monitoring System and Methods of Use"; and U.S. Application No. 61/149,639 entitled "Compact On-Body Physiological Monitoring Device and Methods Thereof", the disclosures of each which are incorporated by reference herein.

Communication Device

In some embodiments, the analyte meter 100 includes an optional communication device (not shown), e.g., a receiver and/or transmitter for communicating with another device, e.g., a medication delivery device and/or a patient monitoring device, e.g., a continuous glucose monitoring device as described above, or a health management system, such as the CoPilot™ system available from Abbott Diabetes Care Inc., Alameda, Calif. The communication device can be configured for wired or wireless communication, including, but not limited to, radio frequency (RF) communication, Zigbee communication protocols, WiFi, Bluetooth communication protocols, and cellular communication, such as code division multiple access (CDMA) or Global System for Mobile communications (GSM).

In one embodiment, analyte meter 100 includes a wireless communication device, wherein the wireless communication device is configured for bi-directional radio frequency (RF) communication with other devices to transmit and/or receive data to and from the analyte meter 100.

In one embodiment, the communication device is configured to include physical ports or interfaces such as a USB port, an RS-232 port, or any other suitable electrical connection port to allow data communication between the analyte meter 100 and other external devices such as a computer terminal (for example, at a physician's office or in hospital environment), an external medical device, such as an infusion device or including an insulin delivery device, or other devices that are configured for similar complementary data communication.

In one embodiment, the communication device is configured for infrared communication, Bluetooth communication, or any other suitable wireless communication mechanism to enable the analyte meter 100 for communication with other devices such as infusion devices, analyte monitoring devices, computer terminals and/or networks, communication enabled mobile telephones, personal digital assistants, or any other communication devices which the patient or user of the analyte meter may use in conjunction therewith, in managing the treatment of a health condition, such as diabetes.

In one embodiment, the analyte meter is configured to wirelessly communicate with a server device, e.g., using a common standard such as 802.11 or Bluetooth RF protocol, or an IrDA infrared protocol. The server device could be another portable device, such as a Personal Digital Assistant (PDA) or notebook computer, or a larger device such as a desktop computer, appliance, etc. In some embodiments, the server device has a display, such as a liquid crystal display (LCD), as well as an input device, such as buttons, a keyboard, mouse or touch-screen. With such an arrangement, the user can control the meter indirectly by interacting with the user interface(s) of the server device, which in turn interacts with the meter across a wireless link.

Input Unit

In some embodiments, analyte meter 100 includes an optional input unit 107 coupled to the housing 105. The input unit can be configured to include one or more input buttons (as shown in FIGS. 1, 3, 5 and 7), a jog wheel, capacitive sensing slider inputs, or combinations thereof. In one embodiment, a user or patient can operate the input unit to perform calculations and determinations associated with one or more medication dose calculation functions, such as a bolus dose calculation function, of the analyte meter 100.

In one embodiment, the input unit includes a plurality of input buttons, wherein each input button is designated for a specific task. Alternatively, one or more of the input buttons can be "soft buttons". In the case where one or more of the plurality of input buttons are "soft buttons", these buttons may be used for a variety of functions. The variety of functions may be determined based on the current mode of the analyte meter 100, and may be distinguishable to a user by the use of button instructions shown on optional display unit 108 of analyte meter 100. Yet another input method may be a touch-sensitive display unit, as described in greater detail below.

In addition, in some embodiments, the input unit 107 is configured such that a user can operate input unit 107 to adjust time and/or date information, as well as other features or settings associated with the operation of analyte meter 100.

Display

In some embodiments, the analyte meter 100 includes an optional display unit 108 or a port (not shown) for coupling an optional display unit to the analyte meter 100. The display unit displays the sensor signals and/or results determined from the sensor signals including, for example, analyte concentration, rate of change of analyte concentration, and/or the exceeding of a threshold analyte concentration (indicating, for example, hypo- or hyperglycemia).

The display unit 108 can be a dot-matrix display. In other embodiments, other display types, such as liquid-crystal displays (LCD), plasma displays, light-emitting diode (LED) displays, or seven-segment displays, among others, may alternatively be used. The display unit 108 can be configured to provide, an alphanumeric display, a graphical display, a video display, an audio display, a vibratory output, or combinations thereof. The display unit can also be configured to provide, for example, information related to a patient's current analyte concentration as well as predictive analyte concentrations, such as trending information.

In some embodiments the input unit 107 and the display unit 108 are integrated into a single unit, for example, the display unit 108 can be configured as a touch sensitive display where the patient may enter information or commands via the display area using, for example, a stylus or any other suitable input device, and where, the touch sensitive display is configured as the user interface in an icon driven environment, for example.

Additional Functional Units

A variety of analyte meters are known in the art, many of which includes additional components and functionalities which can be readily incorporated into the analyte meters described herein. Disclosure of such additional components and functionalities can be found, for example, in U.S. Patent Application Publication No. 2008/0119702, U.S. Patent Application Publication No. US 2008/0114280, and U.S. Patent Application Publication No. 2008/0119710, the disclosure of each of which is incorporated by reference herein.

Demarcation

In one embodiment, an analyte meter according to the present disclosure includes a demarcation that corresponds with a complementary demarcation on an analyte sensor configured to be received by the analyte meter. The use of complementary demarcations on the analyte sensor and meter facilitate insertion of the analyte sensor into the meter in a particular orientation, e.g., a correct orientation. In other words, enables correct registration between an analyte sensor and a meter. A correct orientation is one in which the analyte meter is capable of receiving a sensor signal from the analyte sensor, which signal is indicative of an analyte concentration.

Figure 9:
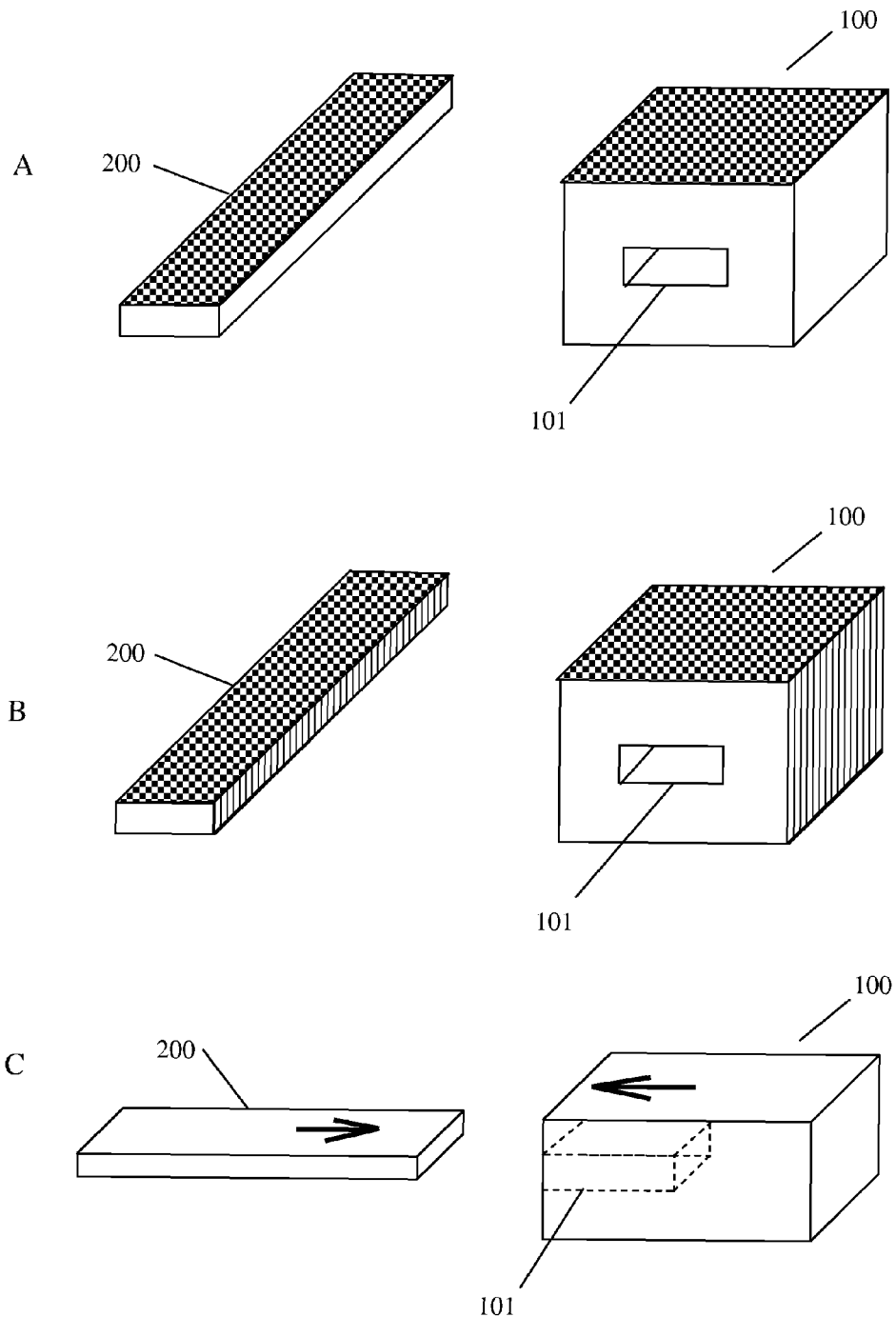
FIG. 9 shows three (A-C) exemplary demarcation schemes according to the present disclosure.

Suitable demarcations include, e.g., colored areas, visible designs or patterns, patterns of indentations, patterns of raised areas, or combinations thereof. The demarcation on the analyte sensor can be the same as a demarcation on the analyte meter. By way of example, FIG. 9, panel A, illustrates an embodiment wherein the top surface of analyte sensor 200 comprises a checkerboard pattern which corresponds to a matching checkerboard pattern present on analyte meter 100. FIG. 9, panel B, illustrates a further embodiment in which analyte sensor 200 and analyte meter 100 have a matching pattern of vertical lines in addition to matching checkerboard patterns.

Corresponding demarcations need not be matching. However, they are configured to convey an insertion orientation to the user. FIG. 9, panel C, for example, shows corresponding arrow designs which are similar except that they point in opposite directions when the analyte sensor is inserted in the intended orientation.

In some embodiments, the analyte sensor includes a first demarcation which includes a first portion of a design or logo, and the analyte meter includes a second demarcation comprising a second portion of the design, such that the first portion of the design mates with the second portion of the design to produce the design when the sensor is correctly inserted into the analyte meter.

Analytes

A variety of analytes can be detected and quantified using the disclosed analyte sensors and meters. Analytes of particular interest include glucose and lactate. Additional analytes that may be determined include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones (e.g., ketone bodies), lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined. Assays suitable for determining the concentration of DNA and/or RNA are disclosed in U.S. Pat. No. 6,281,006 and U.S. Pat. No. 6,638,716, the disclosures of each of which are incorporated by reference herein.

Methods of Using Analyte Meter

The analyte meters described herein find use in methods for determining the concentration of an analyte in a fluid sample from a subject. Generally, these methods include inserting an analyte sensor into an analyte meter 100; contacting a fluid sample e.g. a blood sample, with the analyte sensor; generating a sensor signal at the working electrode; and determining the concentration of the analyte using the generated sensor signal. Examples of specific electrochemical reactions which can be utilized to produce a sensor signal are described in detail in U.S. Pat. No. 6,592,745, the disclosure of which is incorporated by reference herein.

In one embodiment, the analyte sensor is an analyte sensor 200 as described herein. However, it is contemplated that analyte sensors other than those specifically described herein may be configured to operate with the analyte meters 100 disclosed herein. Furthermore, analyte meters can be configured as described herein to be compatible with a variety of analyte sensors.

In one embodiment, the determining step includes determining the concentration of the analyte by amperometry, coulometry, potentiometry, and/or voltametry, including square wave voltametry, using the analyte sensor.

In one embodiment, the determining step includes determining the concentration of the analyte optically. Optical detection of analyte concentration is described, for example, in U.S. Pat. No. 6,592,745, the disclosure of which is incorporated by reference herein.

In one embodiment, the method includes a medication dosage determination step. For example, where the analyte is glucose, the method can include a determination step in which the controller unit performs an algorithm to determine an insulin dose, e.g., a bolus insulin dose, based on the concentration of glucose in the sample.

In another embodiment, the method includes an administering step wherein a medication dose, e.g., an insulin dose, determined according to the method is administered to the subject via a medication delivery device, e.g., a needle, syringe, pump, catheter, inhaler, transdermal patch, or combination thereof.

In another embodiment, the administering step includes administering a medication dose, e.g., an insulin dose, determined according to the method to the subject via a medication delivery device positioned at a distance from the analyte meter and in communication with the analyte meter.

A medication dose, e.g., a bolus dose, determined according to the above methods can be displayed to the user via optional display unit 108 of analyte meter 100.

As discussed previously herein, analyte sensors 200 and analyte meters 100 can be configured for orientation non-specific insertion of the analyte sensor 200 into analyte meter 100. By orientation non-specific insertion, it is meant that either the first substrate or the second substrate can be upward facing when the proximal end of analyte sensor 200 is inserted into the sensor port of a corresponding analyte meter. That is, either the first substrate 201 or the second substrate 202 can be upward facing when the proximal end of the sensor is inserted into analyte meter 100. As such, during a method of using analyte meter 100 with analyte sensor 200, the analyte sensor 200 can be inserted in either of the above orientations without negatively affecting the results of the assay.

Method for Facilitating the Correct Insertion of an Analyte Sensor into an Analyte Meter The present disclosure provides a method for facilitating the correct insertion of an analyte sensor into an analyte meter. In one embodiment, the method includes providing an analyte meter configured to receive an analyte sensor, wherein the analyte meter includes a first demarcation. The method also includes providing an analyte sensor configured for insertion into the analyte meter. The analyte sensor includes a second demarcation which together with the first demarcation indicates an insertion orientation for the analyte sensor.

The demarcations can include, e.g., a color, a design or portion thereof, a pattern of indentations, a pattern of raised areas, or a combination thereof.

In the embodiment shown in FIG. 9, panel A, for example, analyte sensor 200 includes a checkerboard pattern on a first face of analyte sensor 200. This demarcation corresponds to a checkerboard pattern present on a first face of analyte meter 100. Together the demarcations indicate an insertion orientation for the analyte sensor, i.e., checkerboard side up, to a user of the analyte sensor 200 and analyte meter 100. In this embodiment, the demarcations provide a Y-axis orientation for insertion of analyte sensor 200.

FIG. 9, panel B, shows analyte sensor 200 and analyte meter 100, wherein a first face of analyte sensor 200 includes the checkerboard pattern of FIG. 9, panel A, and a second face of analyte sensor 200 includes a pattern of vertical lines. Analyte meter 100 has a first face which includes a corresponding checkerboard pattern and a second face which includes a corresponding pattern of vertical lines. Together the demarcations indicate an insertion orientation for the analyte sensor, i.e., checkerboard side up and vertical lines positioned to the right, to a user of the analyte sensor 200 and analyte meter 100. In this embodiment, the demarcations provide an X and Y-axis orientation for insertion of analyte sensor 200.

FIG. 9, panel C, shows a third embodiment in which analyte sensor 200 includes an arrow design positioned on a first face of analyte sensor 200 towards the proximal end of analyte sensor 200. Analyte meter 100 includes a corresponding arrow design positioned on a first face of analyte meter 100. The arrow designs are positioned such that when analyte sensor 200 is correctly inserted into analyte meter 100 the tips of the arrows appear to be in contact when the analyte sensor and meter are viewed from the top. As with the embodiment of FIG. 9, panel B, the demarcations of this embodiment provide an X and Y-axis orientation for insertion of analyte sensor 200.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An analyte meter, comprising:
   a housing comprising a display;
   a sensor port coupled to the housing, wherein the sensor port is configured to receive a sensor to determine the concentration of an analyte in a fluid sample, and wherein the sensor port comprises a first electrode contact and a second electrode contact; and
   a controller unit coupled to the housing, the controller unit configured to process a signal received from the sensor and determine a concentration of the analyte based on the signal;
   wherein the analyte meter is configured to detect first and second different insertion orientations of the sensor upon insertion of the sensor into the sensor port, and based on the first or second insertion orientation, the analyte meter configures one of the first electrode contact and the second electrode contact as a working electrode contact.

2. The analyte meter of claim 1, wherein each of the first electrode contact and the second electrode contact is also capable of being configured as a reference and/or counter electrode contact, and based on the first or second insertion orientation, the analyte meter configures the first electrode contact as a working electrode contact and the second electrode contact as a reference and/or counter electrode contact.

3. The analyte meter of claim 1, further comprising a third electrode contact.

4. The analyte meter of claim 3, wherein the third electrode contact is capable of being configured as an indicator electrode contact.

5. The analyte meter of claim 3, further comprising a fourth electrode contact.

6. The analyte meter of claim 1, wherein the sensor port is configured to receive a sensor comprising two electrodes.

7. The analyte meter of claim 1, wherein the sensor port is configured to receive a sensor comprising three electrodes.

8. The analyte meter of claim 1, wherein the sensor port is configured to receive a sensor comprising four electrodes.

9. The analyte meter of claim 1, wherein the sensor port is configured to receive a sensor comprising opposing working and reference and/or counter electrodes.

10. The analyte meter of claim 1, wherein the sensor port is configured to receive a sensor comprising coplanar working and reference and/or counter electrodes.

11. The analyte meter of claim 1, wherein the analyte is glucose or ketone bodies.

12. The analyte meter of claim 1, wherein the analyte meter is activated upon insertion of the sensor into the sensor port.

13. The analyte meter of claim 12, wherein the sensor comprises a turn-on/selection monitor, the sensor port comprises a turn-on/selection contact, and the turn-on/selection monitor contacts the turn-on/selection contact upon insertion of the sensor into the sensor port, thereby activating the analyte meter.

14. The analyte meter of claim 13, wherein contact of the turn-on/selection contact with the turn-on/selection monitor opens or closes an electrical circuit, wherein opening or closing of the electrical circuit indicates the insertion orientation of the sensor.

15. The analyte meter of claim 1, wherein the sensor port comprises a first turn-on/selection contact and a second turn-on/selection contact, wherein the first turn-on/selection contact and the second turn-on/selection contact are positioned in an opposing configuration in the sensor port.

16. The analyte meter of claim 1, wherein the analyte meter detects the insertion orientation of the sensor by physical, mechanical, optical, or electrical means.

17. The analyte meter of claim 1, wherein the analyte meter detects the insertion orientation of the sensor by electrical means.

18. The analyte meter of claim 17, wherein the analyte meter detects the insertion orientation of the sensor by detecting the opening of an electrical circuit upon insertion of the sensor into the sensor port.

19. The analyte meter of claim 17, wherein the analyte meter detects the insertion orientation of the sensor by detecting the closing of an electrical circuit upon insertion of the sensor into the sensor port.

20. The analyte meter of claim 1, wherein the controller unit is configured to perform an algorithm to determine a medication dose based on a determined concentration of analyte.

21. The analyte meter of claim 20, wherein the analyte meter further comprises a medication delivery device for administering a medication dose to a subject, wherein the medication dose is determined by the controller unit using the algorithm.

22. The analyte meter of claim 21, wherein the analyte is glucose and the medication is insulin.

23. The analyte meter of claim 21, wherein the medication delivery device comprises a needle, syringe, pump, catheter, inhaler, transdermal patch or combination thereof to deliver the medication.

24. The analyte meter of claim 1, wherein the controller unit is configured to determine the concentration of the analyte by amperometry, coulometry, potentiometry, and/or voltametry using the signal received from the sensor.

25. The analyte meter of claim 1, wherein the controller unit is further configured to determine a bolus dosage based on the signal received from the sensor.

26. The analyte meter of claim 25, further comprising an input unit coupled to the housing, wherein the controller unit is configured to determine the bolus dosage in response to a command received from the input unit.

27. The analyte meter of claim 26, wherein the input unit comprises one or more of an input button, a touch sensitive screen, a jog wheel, or combinations thereof.

28. The analyte meter of claim 1, wherein the display is a touch sensitive display.

29. The analyte meter of claim 1, wherein the display is configured to provide one or more of an alphanumeric display, a graphical display, a video display, or combinations thereof.

30. The analyte meter of claim 1, wherein the controller unit is further configured to determine a bolus dosage based on the signal received from the sensor.

31. The analyte meter of claim 30, wherein the controller unit is further configured to display the determined bolus dosage on the display unit.

32. The analyte meter of claim 31, wherein the displayed bolus dosage is one or more of an alphanumeric display, a graphical display, a video display, an audio display, a vibratory output, or combinations thereof.

33. The analyte meter of claim 11, wherein the analyte meter comprises a receiver and/or transmitter for communicating with a continuous glucose monitor.

34. The analyte meter of claim 11, wherein the analyte meter comprises a receiver and/or transmitter for communicating with a medication delivery device.

35. The analyte meter of claim 1, wherein the analyte meter comprises a communication unit coupled to the housing.

36. The analyte meter of claim 35, wherein the communication unit is a wireless communication unit.

37. The analyte meter of claim 36, wherein the wireless communication unit comprises radio frequency (RF) communication or cellular communication.

38. The analyte meter of claim 35, wherein the communication unit comprises a universal serial bus (USB) port.

39. The analyte meter of claim 35, wherein the communication unit is configured to provide communication with a remote server.

40. A glucose meter, comprising:
a housing comprising a touch sensitive display;
a sensor port coupled to the housing, wherein the sensor port is configured to receive a sensor to determine the concentration of glucose in a fluid sample, and wherein the sensor port comprises a first electrode contact and a second electrode contact;
a controller unit coupled to the housing, the controller unit configured to process a signal received from the sensor and determine a concentration of the glucose based on the signal; and
a communication unit coupled to the housing, wherein the communication unit comprises a universal serial bus (USB) port,
wherein the glucose meter is configured to detect first and second different insertion orientations of the sensor upon insertion of the sensor into the sensor port, and based on the first or second insertion orientation, the glucose meter configures one of the first electrode contact and the second electrode contact as a working electrode contact.

* * * * *